(12) United States Patent
Bourne et al.

(10) Patent No.: US 11,346,543 B2
(45) Date of Patent: May 31, 2022

(54) LIGHT CIRCUIT FOR IMAGING DEVICE

(71) Applicant: Elekta Limited, West Sussex (GB)

(72) Inventors: Duncan Bourne, West Sussex (GB); Gavin Ziyuan Xu, West Sussex (GB); Anthony Williams, West Sussex (GB)

(73) Assignee: Elekta Limited, Crawley (GB)

( * ) Notice: Subject to any disclaimer, the term of this patent is extended or adjusted under 35 U.S.C. 154(b) by 11 days.

(21) Appl. No.: 16/186,036

(22) Filed: Nov. 9, 2018

(65) Prior Publication Data

US 2019/0195487 A1 Jun. 27, 2019

(30) Foreign Application Priority Data

Dec. 21, 2017 (GB) ..................................... 1721680

(51) Int. Cl.
| | | |
|---|---|---|
| *G01R 33/28* | (2006.01) | |
| *F21V 33/00* | (2006.01) | |
| *A61B 5/055* | (2006.01) | |
| *F21V 29/503* | (2015.01) | |
| *F21Y 115/10* | (2016.01) | |
| *F21W 131/20* | (2006.01) | |

(52) U.S. Cl.
CPC .......... *F21V 33/0068* (2013.01); *A61B 5/055* (2013.01); *F21V 29/503* (2015.01); *G01R 33/283* (2013.01); *G01R 33/288* (2013.01); *F21W 2131/20* (2013.01); *F21Y 2115/10* (2016.08)

(58) Field of Classification Search
CPC ... F21V 33/0068; A61B 5/055; G01R 33/283; F21Y 2115/10; F21W 2131/20

USPC ......................................................... 324/322
See application file for complete search history.

(56) References Cited

U.S. PATENT DOCUMENTS

| | | | | |
|---|---|---|---|---|
| 6,598,998 B2* | 7/2003 | West | .................. | G02B 19/0071 362/307 |
| 2005/0162866 A1* | 7/2005 | Osawa | .................... | G02B 6/009 362/612 |
| 2005/0254256 A1* | 11/2005 | Gosswein | .............. | G01R 33/28 362/572 |
| 2006/0061432 A1* | 3/2006 | Hsu | ....................... | H05K 1/0219 333/33 |

(Continued)

OTHER PUBLICATIONS

"United Kingdom Application Serial No. GB1721680.5, Search and Examination Report dated Jun. 29, 2018", (Jun. 29, 2018), 7 pgs.

*Primary Examiner* — Jermele M Hollington
*Assistant Examiner* — Courtney G McDonnough
(74) *Attorney, Agent, or Firm* — Schwegman Lundberg & Woessner, P.A.

(57) ABSTRACT

A medical imaging device having a bore 104 for receiving a patient during a medical imaging process and a ventilation channel 216 having an opening within the upper circumference of the bore for supplying cool air into the bore. At least one lighting circuit 210 with one or more LEDs is positioned within the ventilation channel 216 and is configured to illuminate the entire length of the bore 104. Air supplied from the ventilation channel 216 cools the lighting circuit 210 and prevents overheating effects within the lighting circuit that are caused by fields generated during the medical imaging process. The lighting circuit 210 comprises one or more filters, wherein the resonance frequency of the medical imaging device is within the stopband of the filters.

20 Claims, 4 Drawing Sheets

(56) References Cited

U.S. PATENT DOCUMENTS

2012/0302833 A1  11/2012  Hayman et al.
2017/0281043 A1* 10/2017  Shvartsman ......... A61N 5/1049

* cited by examiner

LIGHT CIRCUIT FOR IMAGING DEVICE

CLAIM FOR PRIORITY

This application claims the benefit of priority of United Kingdom Application Serial No. 1721680.5, filed Dec. 21, 2017, which is hereby incorporated by reference in its entirety.

TECHNICAL FIELD

The present disclosure generally relates to apparatuses and methods for medical imaging. Examples of the disclosure include, without limitation, apparatuses and methods for lighting the interior bore of a medical imaging device.

BACKGROUND

Medical imaging devices are used for collecting and providing image data of a patient. These imaging devices provide valuable information about the internal anatomy of the patient's body. Examples of imaging devices include magnetic resonance imaging (MRI) devices, computed tomography (CT) devices, ultrasound imaging devices, PET imaging devices, and SPECT imaging devices.

Many imaging devices include a hollow bore into which a subject is placed, usually in the supine position, for the duration of the imaging process. This bore is typically cylindrical and is formed by an inner wall within the imaging device housing. Within the housing and surrounding the bore, there are the components of the imaging device used to perform the imaging process. For example, in an MRI system, the housing may contain one or more magnets and coils for generating a magnetic field and for collecting the measurement signals emitted from the patient's body.

For the imaging device to collect high-quality image data, the patient generally needs to remain motionless within the bore for an extended period of time. However, the bore may be uncomfortable for the patient. For example, because it is usually advantageous to bring the imaging components of the device as close to the patient as possible (e.g., to improve signal-to-noise ratio), many imaging devices have narrow bores that are difficult to illuminate once a patient is placed inside. This may cause some patients to feel discomfort and anxiety, and to move as a result, thus affecting image quality.

To increase patient comfort, some imaging devices provide light sources outside the bore and attempt to direct the emitted light into the bore using light guides. These light sources may include electric light sources, such as halogen lamps. However, such arrangements have drawbacks because the process of guiding the exterior light into the bore is often inefficient. As a result, these types of arrangements usually employ a very powerful light source to provide only an average amount of illumination within the bore. These powerful light sources are typically expensive and have a short life span, making replacements both frequent and expensive. But even with a new light source, it is still difficult to achieve a suitably diffused and homogeneous lighting effect within the bore at a level that will comfort the patient.

Imaging systems having light sources within the bore have so far been inadequate. As known in the field, the imaging process will typically damage a light source situated within the bore. For example, the radiofrequency (RF) fields of an MRI system would damage a standard LED strip in the system's bore because the RF fields, during imaging, would induce a high frequency current in the LEDs, causing them to overheat and, ultimately, irreparably fail. Such an LED strip would also not effectively light the bore because the light would point down towards the patient, instead of running along the entire bore length. Additionally, the placement of a metallic light component in the bore of an MRI system would distort the magnetic field, thus hampering image quality.

An additional consideration associated with placement of light sources within the bore of an imaging device is the potential to affect the specific absorption rate (SAR). SAR indicates the potential for heating the patient's tissue due to application of RF fields during imaging (e.g., during an MRI scan). Increases in an SAR dose may present a safety concern for patients, who may experience localized heating and burns when the SAR dose becomes too large at a particular tissue location. Light sources such as LED strips include conductive components, such as traces, which can interact with RF fields and change their linearity within the bore of an imaging device. This may result in inhomogeneity of the RF fields, thus changing the SAR and breaching the maximum SAR dose permitted during imaging.

Recent efforts have also been made to combine imaging devices with therapy devices to allow improved imaging of the patient's body during therapy. For example, Elekta's "Unity" MR-RT system provides MR images during radiotherapy, improving visibility of the patient's body during therapy and allowing for more effective targeting of features, such as tumours. However, the problem of insufficient lighting of the imaging device bore remains unsolved.

Embodiments of the present disclosure provide an improved solution to light the bore of an imaging device.

SUMMARY

Disclosed herein is an apparatus and method for illuminating the bore of a medical imaging device. Particular examples of the disclosure disclose a medical imaging device that includes a lighting circuit placed within the housing of the medical imaging device without overheating.

In accordance with a first aspect, a medical imaging device for imaging a patient during a medical imaging process is provided. The medical imaging device includes a housing, a ventilation channel, and at least one lighting circuit. The housing includes a bore extending in a lateral direction between a proximal end and a distal end, the bore configured to accommodate at least a portion of a patient extending in the lateral direction during the medical imaging process. A cross-section of the bore has a circumference. The housing further includes an imager configured to generate images of the patient as the patient extends in the lateral direction within the bore. The ventilation channel has an opening within the bore, wherein the opening extends around at least a portion of the bore circumference. The at least one lighting circuit is positioned within the ventilation channel and configured to illuminate the bore. The ventilation channel is configured to allow air to pass through the ventilation channel and over the at least one lighting circuit.

In accordance with a second aspect, a lighting circuit is provided. The lighting circuit may be positioned within a ventilation channel of a medical imaging device. The lighting circuit may include a printed circuit board and one or more light emitting diodes mounted on the printed circuit board. At least one light emitting diode has a direction of light emission that is parallel to the plane of the printed circuit board.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

Embodiments will now be described, purely by way of example, with reference to the accompanying drawings, wherein like elements are indicated using like reference signs, and in which.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Figure 1:
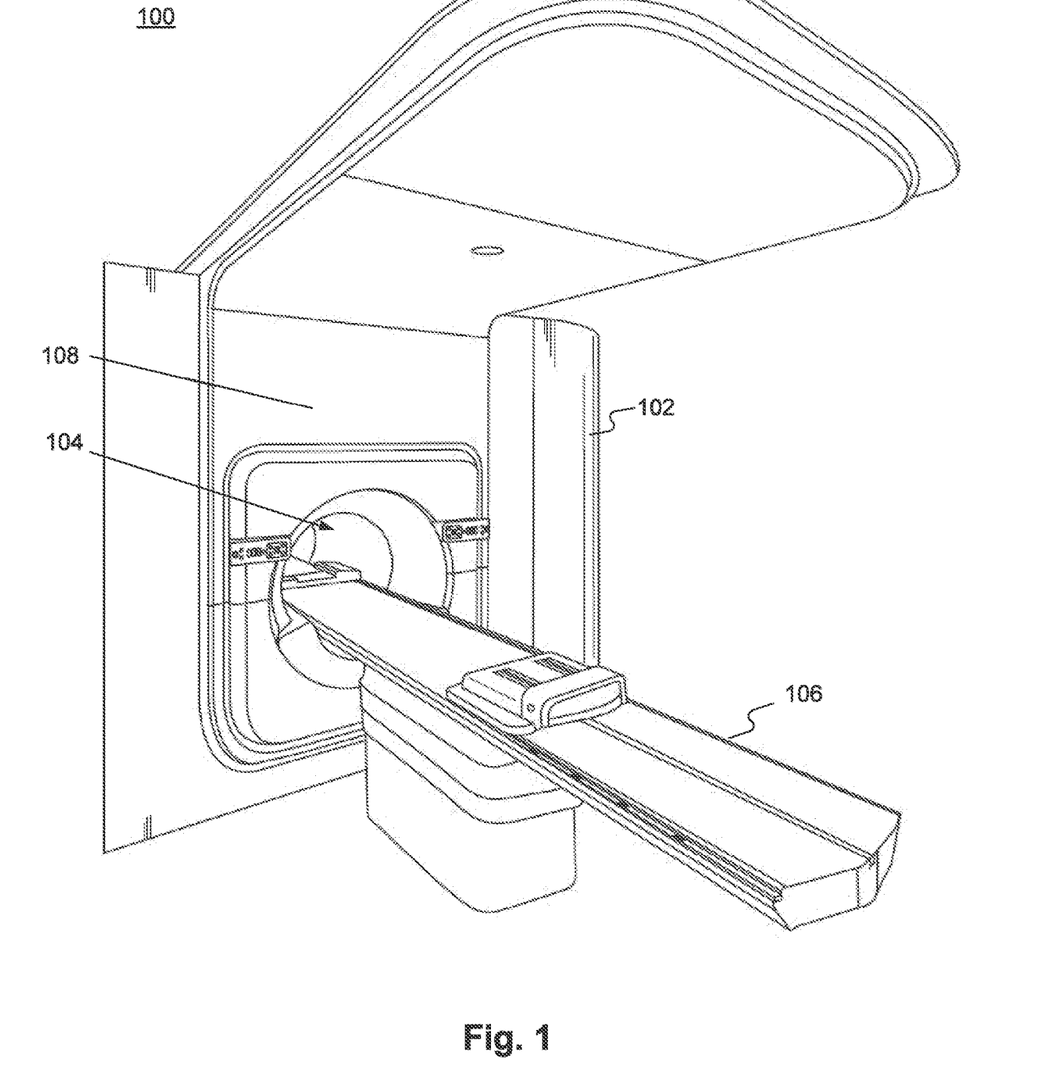
FIG. 1 is a front view of an exemplary medical imaging device.

FIG. 1 is a front view of an exemplary medical imaging device 100. Imaging device 100 may be a magnetic resonance imaging (MRI) device, a computed tomography (CT) device, an ultrasound imaging device, a PET imaging device, or a SPECT imaging device. Imaging device 100 may also be the imaging component of a combination imaging and therapy system. For example, imaging device 100 may be an MRI device within a MR-linear accelerator (MR-LINAC) system. However, it will be appreciated that the application of the disclosed embodiments is not limited to MRI, CT, ultrasound, PET, SPECT, or MR-LINAC, and that the apparatuses and methods disclosed herein may be used to enable any suitable medical imaging device or any suitable combination medical imaging and therapy system.

Imaging device 100 may include a housing 102 with a hollow bore 104 which may extend from front face 108 of housing 102 to the rear face (not depicted in FIG. 1) of housing 102. In some embodiments, when the patient is positioned within bore 104, the patient's head may be positioned near front face 108 and the patient's feet may be positioned near the rear face of housing 102. Bore 104 may be accessed from either front face 108 or from the rear face of housing 102. Bore 104 may be cylindrical and is formed by an inner wall of housing 102. However, bore 104 may have other shapes or configurations, such as rectangular, oval, etc. For at least a cylindrical configuration, bore 104 may have a diameter large enough to accommodate both a patient and patient support 106. Bore 104 has a longitudinal axis that extends the entire length of bore 104, running parallel to the inner wall of housing 102 from front face 108 to the rear face of housing 102.

Housing 102 may additionally include internal components mounted therein which may be used for performing an imaging process, a therapy process, or a combination imaging-therapy process. These internal components may be situated within housing 102 so as to at least partially surround bore 104, allowing use of the internal components for imaging a patient or subject placed within bore 104. The internal components may be used to image a portion of the patient's body or the entirety of the patient's body. For example, the internal components may include one or more magnets and coils for generating a magnetic field and for receiving the measurement signal emitted by the patient's body (e.g., as in an MRI system). Alternatively, the internal components may include one or more x-ray sources for irradiating the patient's body, as well as one or more radiation detectors. The internal components may also include any other components used in a medical imaging device. The internal components may additionally include components which may be used for therapy, such as one or more therapeutic RF sources.

Imaging device 100 may additionally include patient support 106, which may be configured to support the patient's body or a portion thereof. For example, the patient may assume a supine position upon patient support 106. Patient support 106 may be movable relative to housing 102 in at least three coordinate axial directions with respect to the longitudinal axis of bore 104. Support 106 may also rotate, such as around its support or around bore 104's longitudinal axis. To illustrate, before the imaging process begins, the patient may assume a supine position upon patient support 106. After that, patient support 106 may be moved into bore 104 until the patient is correctly positioned for the imaging process and, if desired, for a therapy process.

Figure 2:
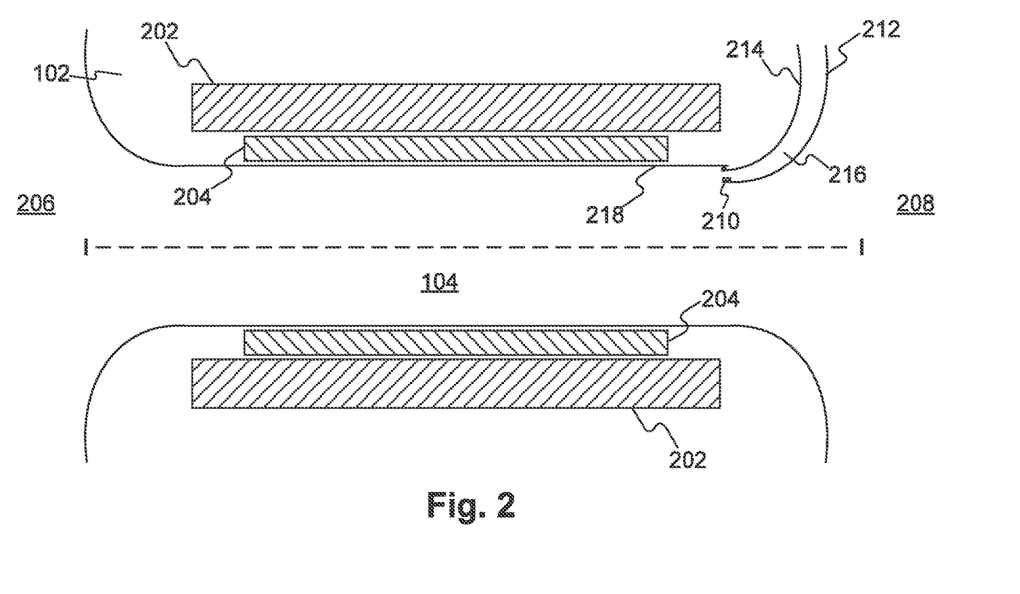
FIG. 2 is a cross-sectional view of an exemplary medical imaging device.

FIG. 2 is a cross-sectional view of an exemplary medical imaging device 100. Bore 104 is situated within housing 102 such that bore 104 extends from bore front 206 to bore rear 208. In some embodiments, bore front 206 may be situated on the same side of housing 102 as front face 108. Bore 104 may be at least partially surrounded by bore wall 218, which may be the innermost wall of housing 102. Bore wall 218 may be cylindrical and may extend the entire length of bore 104. An RF coil 204 and main field and gradient coils 202 may be situated within housing 102 and may at least partially surround bore 104. Field and gradient coils 202 may be positioned radially outwards from RF coil 204 with respect to a longitudinal axis I. As known in the art, during an MR imaging process, field and gradient coils 202 may be used to generate varying magnetic field gradients. RF coil 204 may be used to generate an RF field which excites nuclei in the patient's body. RF coil 204 may also be used to sense resonance signals emitted by the excited nuclei, which may be used to generate medical image data.

In example embodiments consistent with the present disclosure, a ventilation channel 216 may be located at the distal end of bore 104, in proximity to bore rear 208 and to the rear face of housing 102. Alternatively or additionally, ventilation channel 216 may be situated at the proximal end of bore 104, in proximity to bore front 206 and to the front face of housing 102. Ventilation channel 216 may be an annular channel and may at least partially surround bore 104. Ventilation channel 216 may extend circumferentially along at least a portion of bore wall 218. Ventilation channel 216 may be formed between a first duct portion 212 and a second duct portion 214. First 212 and second 214 duct portions may be separate and distinct structures. Ventilation channel 216 may supply air into bore 104. For example, ventilation channel 216 may supply cool air into bore 104 to cool bore 104 and the patient positioned therein.

A lighting circuit 210 may be positioned at least partially within ventilation channel 216, in proximity to the outlet of ventilation channel 216 into bore 104. In some embodiments, lighting circuit 210 may be situated upon or coupled to first duct portion 212. Lighting circuit 210 may be entirely contained within the profile of the ventilation channel. For example, lighting circuit 210 may be positioned entirely within ventilation channel 216 in such a manner that no portion of the lighting circuit extends out of the ventilation channel into bore 104. In some embodiments, the section of first duct portion 212 which forms the outlet into bore 104 may be positioned radially inwards from bore wall 218, relative to longitudinal axis I. Lighting circuit 210 may also be situated upon or otherwise coupled to this section of first duct portion 212, such that lighting circuit 210 may also be positioned radially inwards from bore wall 218, relative to longitudinal axis I. As a result, air from ventilation channel 216 may be delivered into bore 104 along a direction substantially parallel to or slightly diverging from longitudinal axis I, such that the air may flow along the entire longitudinal length of bore 104. Additionally, this may allow light emitted by lighting circuit 210 to be directed into bore 104 in a direction which is substantially parallel to longitudinal axis I, as well as to bore wall 218. For example, according to embodiments in which ventilation channel 216 is positioned near bore rear 208, light from lighting circuit 210 may be directed towards bore front 206, along a direction substantially parallel to longitudinal axis I. As a result, the entire longitudinal length of bore 104 may be illuminated by lighting circuit 210, without any feature in bore 104 obstructing or otherwise blocking the emitted light. As a result, there is no need to place lights along the entire length of bore 104. This can reduce the number of lights needed to illuminate bore 104.

In some embodiments, a single lighting circuit 210 may be positioned at least partially within ventilation channel 216, such as in the arrangement described above. In alternative embodiments, a plurality of lighting circuits 210 may be positioned at least partially within ventilation channel 216. For example, two or more lighting circuits 210 (e.g., two, three, four, five, eight, ten, or more lighting circuits 210) may be arranged circumferentially relative to longitudinal axis I, such that each lighting circuit 210 may be positioned at a different angle relative to longitudinal axis I. Additionally or alternatively, two or more lighting circuits 210 may be positioned at different longitudinal positions relative to longitudinal axis I. For example, two or more lighting circuits may be positioned side-to-side within ventilation channel 216. Additionally or alternatively, according to embodiments in which medical imaging device 100 includes multiple ventilation channels 216, at least one lighting circuit 210 may be positioned within each ventilation channel 216. The light emitted by lighting circuit 210 may also be diffusely reflected by bore wall 218. In some embodiments, at least a portion of bore wall 218 may be coated with paint with a specified gloss. For example, at least a portion of bore wall 218 may be coated with a white paint with 40%-60% gloss. In some embodiments, at least a portion of bore wall 218 may be coated with a white paint with 50% gloss. Advantageously, such a paint may reflect incident light into bore 104 without blinding the patient or creating a glare.

This may provide homogenous illumination of bore 104 along the height and width dimensions. As a result, the entire bore volume may be evenly illuminated by lighting circuit 210. This is an improvement over the prior art light guides that only illuminate a small portion of the bore, leaving the remainder dark. Additionally, in some embodiments, one or both of the proximal and distal ends of bore 104 may taper inwards. For example, one or both of the portions forming bore front 206 and bore rear 208 may have a reduced inner diameter, as compared to the diameter of bore wall 218. As a result, light emitted by lighting circuit 210 may be incident upon at least one tapered end and reflected back into bore 104 as opposed to, for example, passing outside of bore 104. In this way, the illumination of bore 104 may be enhanced by light reflected by one or both tapered ends.

In some embodiments, the placement of lighting circuit 210 within ventilation channel 216 may allow for lighting circuit 210 to be cooled by the air supplied by ventilation channel 216. As a result, any current induced within lighting circuit 210 by the imaging process will not cause heating or destruction of any component of lighting circuit 210 because any heating caused by this current will be negated by the cool air from ventilation channel 216. In the example where the medical imaging device is an MRI system, lighting circuit 210 would not be overheated or destroyed by the heating effect of the RF fields because lighting circuit 210 is cooled by the air supplied by ventilation channel 216 and lighting circuit 210 is not inside bore 104. If such a lighting circuit were instead attached directly to bore wall 218 or positioned within a dedicated channel without ventilation, lighting circuit 210 may fail prematurely due to insufficient cooling to counteract any heating caused by the imaging process.

The placement of lighting circuit 210 within ventilation channel 216 may also give bore 104 a neater appearance because lighting circuit 210 may be less conspicuous than if it were attached directly to bore wall 218. Because of its placement within ventilation channel 216, lighting circuit 210 may be less noticeable or obstructive to a patient positioned within bore 104 than if it were attached directly to bore wall 218. Additionally because lighting circuit 210 may be wholly contained within ventilation channel 216, it does not extend into bore 104. This may prevent lighting circuit 210 from taking up space within bore 104 or from reducing the amount of space that is available to the patient within bore 104.

The placement of lighting circuit 210 within ventilation channel 216 may also provide the additional benefit of providing longitudinal distance between lighting circuit 210 and RF coil 204. Lighting circuit 210 may be positioned at the distal end of bore 104 away from RF coil 204, which may not extend to the distal end of bore 104. This longitudinal distance between lighting circuit 210 and RF coil 204 reduces the currents that may be induced in lighting circuit 210 by the RF field generated by RF coil 204. As a result, the risk of damage to lighting circuit 210 by the RF field may be further minimized. Additionally, the distance between lighting circuit 210 and RF coil 204 may reduce the risk of the metal components of lighting circuit 210 interacting with the RF field, which may degrade the quality of images generated by the medical imaging device.

Figure 3:
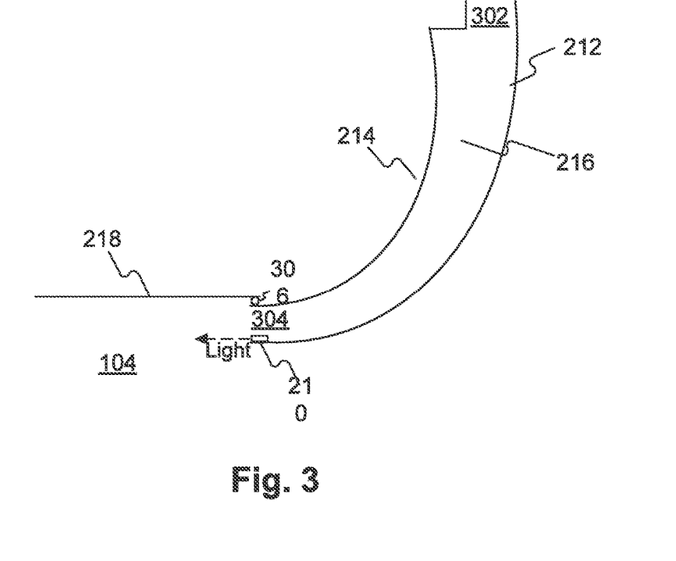
FIG. 3 is a more detailed view of FIG. 2 showing an exemplary position of a lighting circuit within a ventilation channel.

FIG. 3 is a detailed view of FIG. 2 showing an exemplary position of a lighting circuit 210 within a ventilation channel 216. Ventilation channel 216 may be formed by first duct portion 212 and second duct portion 214 and may have an air inlet 302 at a first end thereof and an outlet at a second end thereof, at the position of an opening 304 into bore 104. Inlet 302 may be positioned radially outwards from opening 304, with respect to longitudinal axis I and bore 104, such that inlet 302 may be situated at an outer end of ventilation channel 216 and opening 304 may be positioned at an inner end of ventilation channel 216. Opening 304 may open into bore 104 such that air within opening 304 may flow into bore 104, and vice versa. Ventilation channel 216 may additionally be curved between inlet 302 and opening 304. According to embodiments in which ventilation channel 216 is positioned in proximity to bore rear 208, channel 216 may curve towards bore front 206 as it extends from inlet 302 to opening 304. As a result, opening 304 may be positioned in closer proximity to bore front 206 than inlet 302. According to embodiments in which ventilation channel 216 is positioned in proximity to bore front 206, channel 216 may similarly curve towards bore rear 208. Inlet 302 may be connected to a pump (not shown) so as to create forced movement of air through ventilation channel 216 and into bore 104. For example, the pump may create forced movement of cool air through channel 216. The air may flow from inlet 302, along ventilation channel 216, and may exit into bore 104 via opening 304. Lighting circuit 210 may be positioned in opening 304 so that the cool air flows along lighting circuit 210 and cools circuit 210, thereby preventing failure of lighting circuit 210 by the components of the imaging device 100 that are used during the imaging process. In some embodiments, an air-tight seal 306 is provided between bore wall 218 and second duct portion 214 to prevent passage of air, liquid, or any contaminants between the two.

In some embodiments, lighting circuit 210 may contain one or more light sources mounted upon a flexible printed circuit board (PCB) so as to form a lighting strip. For example, lighting circuit 210 may contain one or more LEDs. The LEDs may be right-angled LEDs so that light emitted by the LEDs may radiate in a direction that is parallel to longitudinal axis I. Because lighting circuit 210 is positioned radially inwards from bore wall 218 with respect to longitudinal axis I, the emitted light may be directed along the entire length of bore 104 without obstruction, thereby illuminating the entire length of bore 104.

Figure 4:
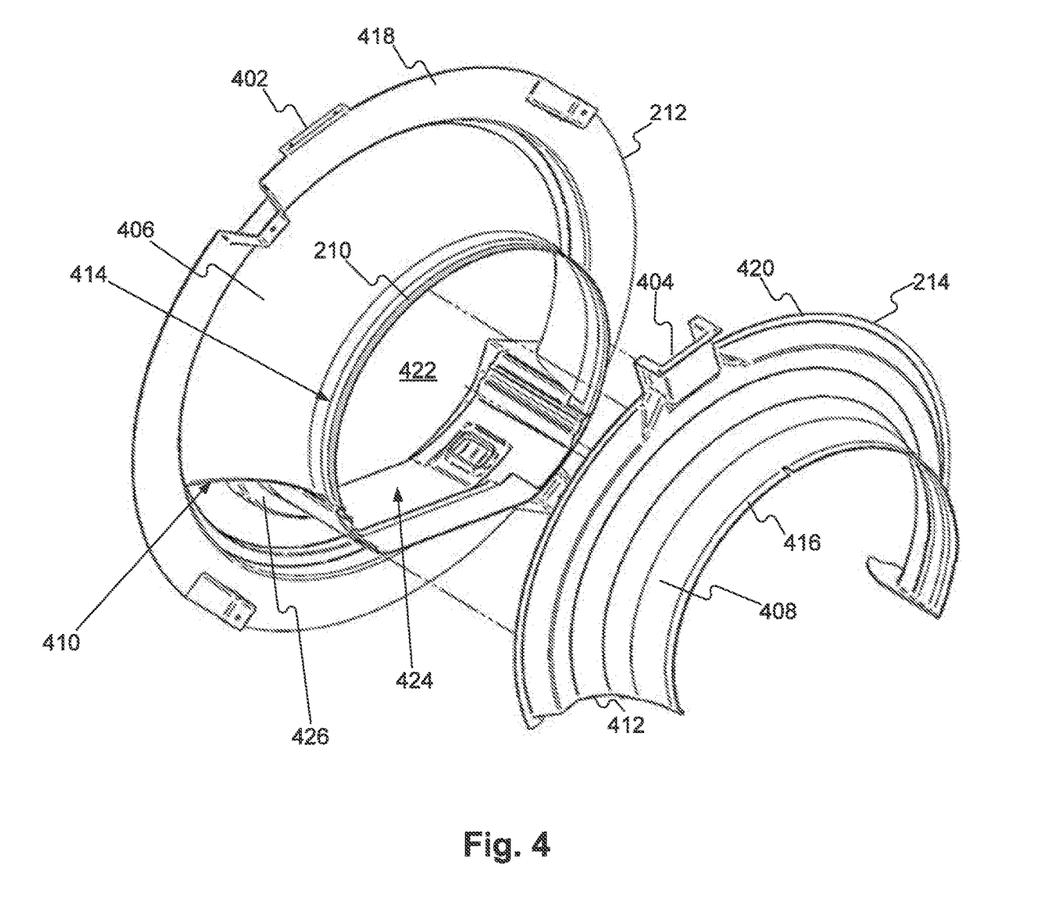
FIG. 4 is a detailed view of exemplary first and second duct portions.

FIG. 4 is a detailed view of exemplary first and second duct portions 212 and 214. In the example of FIG. 4, first and second duct portions 212 and 214 are described according to embodiments in which ventilation channel 216 is positioned near bore rear 208. However, one of ordinary skill in the art will understand that first and second duct portions 212 and 214 may additionally or alternatively be similarly configured to form a ventilation channel 216 in proximity to bore front 206. First duct portion 212 may be substantially cone-like in shape, with a first opening portion 414 at its proximal end that may face bore 104 and a larger-diameter first seal end 418 at its distal end that may face towards the rear face of housing 102. A first vent face 406 may extend between the proximal and distal ends of first duct portion 212. First vent face 406 may gradually decrease in diameter as it extends from the distal end to the proximal end. A cone opening 422 may extend through first duct portion 212. Cone opening 422 may be situated at the distal end of bore 104 and may have a slightly reduced cross-sectional area relative to bore 104. When first and second duct portions 212 and 214 are positioned at the distal end of bore 104, bore 104 may be accessed via cone opening 422. Lighting circuit 210 may be positioned upon or otherwise secured to the outer surface of first opening portion 414, relative to longitudinal axis I. Additionally, lighting circuit 210 may extend circumferentially along at least a portion of the outer surface of first opening portion 414. In some embodiments, at least one lighting circuit 210 may extend along the entire circumferential length of the outer surface of first opening portion 414. In alternative embodiments, a plurality of lighting circuits 210 may be situated upon the outer surface of first opening portion 414, each extending along a separate circumferential portion thereof. In such embodiments, the lighting circuits 210 may collectively cover most or all of first opening portion 414.

In some embodiments, second duct portion 214 may be semi-circular and may have a second opening portion 416 at its proximal end and a larger-diameter second seal end 420 at its distal end. A second vent face 408 may extend between the proximal and distal ends of second duct portion 214. In some embodiments, second vent face 408 may gradually decrease in diameter as it extends from the distal end to the proximal end. Second opening portion 416 may have an outer diameter which is substantially equal to the inner diameter of bore wall 218, with seal 306 optionally positioned between them.

In some embodiments, second duct portion 214 may be disposed upon first duct portion 212 in a telescoping arrangement in which second duct portion 214 is positioned upon first duct portion 212. In this way, first seal end 418 may be located adjacent to second seal end 420, and first opening portion 414 may be situated radially inwards from second opening portion 416, with a gap therebetween. First 212 and second 214 duct portions may be secured relative to each other using any suitable means. For example, first 212 and second 214 duct portions may be secured by one or more of screws, clips, bonding, or by other known securing mechanisms.

In some embodiments, inlet 302 of ventilation channel 216 may be formed between first inlet portion 402 of first duct portion 212 and second inlet portion 404 of second duct portion 214. First inlet portion 402 may be an opening within the first seal end 418. Alternatively or additionally, the second inlet portion 404 may be an opening within the second seal end 420. First seal end 418 and second seal end 420 may be secured in an air-tight arrangement. For example, air may enter the top of ventilation channel 216 via the inlet formed between first and second inlet portions 402 and 404.

In some embodiments, the body of ventilation channel 216 may be formed by a gap that extends between first and second vent faces 406 and 408. Accordingly, first and second vent faces 406 and 408 may not be positioned immediately adjacent to each other, but may instead have the gap between them. First vent face 406 may have a first side portion 410 at either side thereof. Similarly, second vent face 408 may have a second side portion 412 at either side thereof. The sides of ventilation channel 216 may be formed by first and second side portions 410 and 412. In some embodiments, first and second side portions 410 and 412 may be secured together in an air-tight arrangement. Accordingly, ventilation channel 216 does not extend around the entire circumference of bore 104. Instead, it may extend circumferentially about the portion of bore wall 218 that overlaps with second duct potion 214.

In some embodiments, opening 304 of ventilation channel 216 may be formed by a gap that extends between first and second opening portions 414 and 416. Opening 304 may extend around the same portion of the circumference of bore 104 as does ventilation channel 216. Lighting circuit 210 may be positioned upon or otherwise secured to first opening portion 414 of first duct portion 212. For example, an adhesive may be used to attach the lighting circuit to the first opening portion. In some embodiments, first opening portion 414 may be parallel to bore wall 218. As a result, the lighting circuit may also be positioned parallel to the bore wall when the lighting circuit is positioned upon the first opening portion. This allows the light emitted by the right-angled LEDs of the lighting circuit to be directed parallel to the bore wall along the entire length of the bore.

In some embodiments, first duct portion 212 may include a patient portion 424, which may be situated at the bottom of cone opening 422. In some embodiments, patient portion 424 may be substantially flat and configured to support the patient and/or patient support 106. For example, during imaging and/or therapy the patient may lie supine upon patient support 106 and face upwards towards ventilation channel 216. Accordingly, ventilation channel 216 and opening 304 may extend around an upper portion of the circumference of bore 104. Lighting circuit 210 may extend around substantially the entire ventilation channel 216. Therefore, lighting circuit 210 may also extend circumferentially around the same upper portion of bore 104. This may provide a greater amount of light and a more even distribution of that light.

In some embodiments, power to lighting circuit 210 may be supplied by a cable. For example, the cable may be routed through ventilation channel 216. The direction in which the cable is routed may minimize electromagnetic coupling between the RF field and the cable, which may additionally help to avoid damage to lighting circuit 210.

In some embodiments, a sealed chamber 426 may be positioned beneath patient portion 424. Sealed chamber 426 may be sealed in an air-tight and/or liquid-tight arrangement. As a result, any bodily fluids which may present themselves within bore 104 (e.g. blood, urine and vomit) will not leak into sealed chamber 426. Additionally, because ventilation channel 216 and lighting circuit 210 are positioned above the patient, they will not come in contact with any bodily fluids the patient may discharge while in bore 104. This allows the imaging device 100 to be kept in a hygienic state and prevents damage of ventilation channel 216 and/or lighting circuit 210 by bodily fluids.

Figure 5:
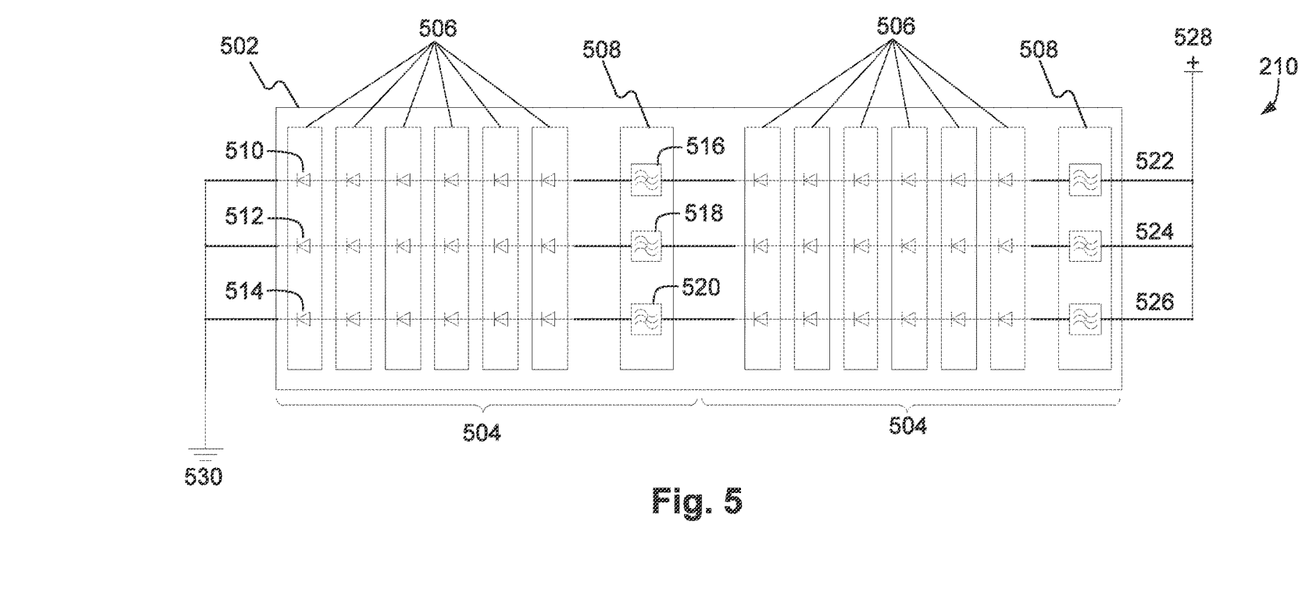
FIG. 5 is a schematic diagram of an exemplary lighting circuit.

FIG. 5 is a schematic diagram of an exemplary lighting circuit 210. Lighting circuit 210 may include a strip 502 which may include a flexible PCB with one or more modules 504 mounted thereon. One of ordinary skill in the art will understand the term "flexible" to mean the PCB is capable of bending without breaking or fracture. This capability may be due, at least in part, to the material composition of the PCB. For example, the PCB may be constructed of a flexible material such as polyimide, polyether ether ketone, polyester, polyethylene naphthalate, polyetherimide, fluropolymers, and copolymers. In some embodiments, the PCB is sufficiently flexible so as to allow strip 502 be bent and fitted into ventilation channel 216 without fracturing or being damaged. In some embodiments, each module 504 may include one or more light emitting diodes (LEDs) 506 connected in series with a filter 508.

According to embodiments in which strip 502 contains a plurality of modules 504, each filter 508 may be connected in series between the LEDs of two adjacent modules. As a result, current flowing out of LEDs 506 of a first module 504 will first flow through filter 508 of the next module 504 before flowing to LEDs 506 of the next module. LEDs 506 within each module 504 are also connected together in series. In the embodiment of FIG. 5, each group of one or more LEDs 506 may include six LEDs. However, it is contemplated that any desired number of LEDs may be used within each module. The number of modules 504 included within strip 502 may be determined according to the desired strip length. For example, when fitting strip 502 within ventilation channel 216, a user may determine the length of ventilation channel 216 along which lighting circuit 210 is to be situated. The user may include the number of modules 504 within strip 502 which result in strip 502 achieving this desired length. Strip 502 may include one or more modules 504. In some embodiments, strip 502 is connected with current source 528, which provides current to strip 502 to power the various components therein, and with common ground 530.

In some embodiments, LEDs 506 may be RGB LEDs. RGB LEDs may be used because they can be controlled to achieve a specific colour that may be aesthetically pleasing and soothing to the patient positioned within bore 104 of imaging device 100. LEDs also have the additional benefit of lasting longer than halogen bulbs placed outside imaging device 100. Each of the RGB LEDs may include at least one red-emitting diode 510, at least one green-emitting diode 512, and at least one blue-emitting diode 514. Red-emitting diode 510 of each individual LED may be connected in series with red-emitting diodes of the other LEDs mounted upon strip 502. These red-emitting diodes may be connected in series via power input line 522, which may extend from current source 528 to common ground 530 without connection to diodes of any other colour. The green-emitting diode 512 and blue-emitting diode 514 of each LED may be similarly connected via power lines 524 and 526, respectively. In some embodiment, current source 528 may provide current to power input lines 522, 524, and 526 through converters and/or inverters controlled using pulse width modulation (PWM). This may allow current source 528 to control the current in each of power input lines 522, 524, and 526 to achieve a desired colour of LEDs 506. Power input lines 522, 524, and 526 may share a common ground 530, which can protect strip 502 and all of the components mounted thereon from interference from external devices, such as the components of imaging device 100 used to perform the imaging process, components of imaging device 100 used to perform a therapy process, and current source 528.

In some embodiments, each filter 508 may include filters 516, 518, and 520, each of which may be connected to one of power input lines 522, 524, and 526. For example, current flowing along power input line 522 from red-emitting diodes 510 of a first module 504 may first flow through filter 516 of the next module before flowing to the red-emitting diodes of the next module. Similarly, current in power input line 524 flowing between green-emitting diodes 512 in two consecutive modules may flow through filter 518 in the second of the two modules, and current in power line 526 flowing between blue-emitting diodes 514 in two consecutive modules may flow through filter 520 in the second of the two modules. In some embodiments, filters 516, 518, and 520 may be simple passive RLC filters with an air core inductor.

In some embodiments, filters 516, 518, and 520 may be tuned based on the resonant frequency of imaging device 100. For example, if imaging device 100 is an MRI system, filters 516, 518, and 520 may be tuned to the frequency of RF fields generated by the MRI. That is, the MRI resonant frequency is included in the filter stopband of filters 516, 518, and 520. In some embodiments, imaging device 100 may include a resonant frequency of about 64 MHz. Accordingly, the filter stopband of filters 516, 518, and 520 may be configured to include frequencies spanning a range of about 60 MHz and about 70 MHz. In other embodiments, the filter stopband of filters 516, 518, and 520 may be configured to include frequencies spanning a range of about 62 MHz and about 66 MHz. In some alternative embodiments, imaging device 100 may include a resonant frequency of about 128 MHz. Accordingly, the filter stopband of filters 516, 518, and 520 may be configured to include frequencies spanning a range of about 122 MHz and about 132 MHz. In other embodiments, the filter stopband of filters 516, 518, and 520 may be configured to include frequencies spanning a range of about 126 MHz and about 130 MHz. As a result, filters 516, 518, and 520 may minimize current in lighting circuit 210 that is induced by the imaging process because this current would be induced at the MRI resonant frequency. In addition to the cooling provided by the ventilation channel, this filtering provides the lighting circuit additional protection against overheating caused by the imaging process. Specifically, this filtering may prevent damage to LEDs 506. However, because the PWM frequency is different from the MRI resonant frequency, filters 516, 518, and 520 may not attenuate current from current source 528 and therefore will not affect the light colour and light intensity of LEDs 506. By minimizing heating, filters 516, 518, and 520 may provide the additional benefit of extending the lifetime of components within lighting circuit 210 and minimizing the replacement frequency.

Figure 6:
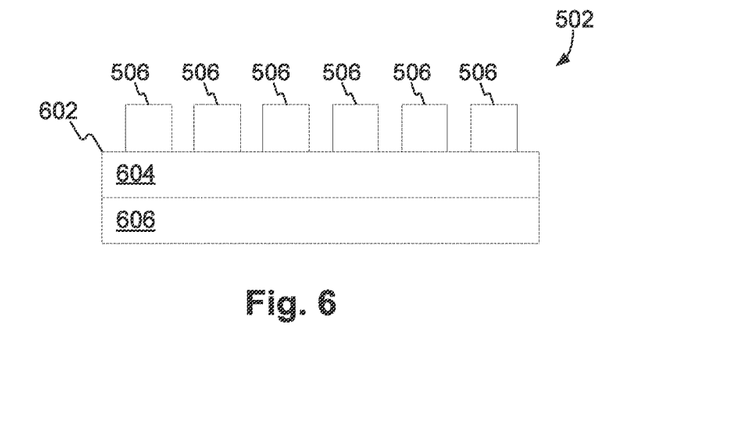
FIG. 6 is a front view of an exemplary lighting strip.
Figure 7:
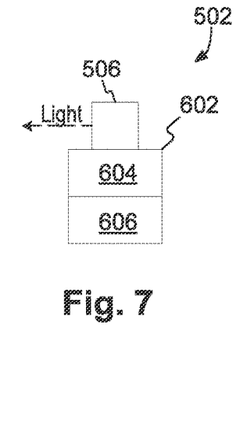
FIG. 7 is a side view of an exemplary lighting strip.

FIG. 6 is a front view of an exemplary strip 502. FIG. 7 is a side view of an exemplary strip 502. Strip 502 may include flexible PCB 602 and one or more LEDs 506. In some embodiments, PCB 602 is a two layer flexible PCB and may include two signal layers 604 and 606. Layers 604, 606 may be separate and distinct layers and may be connected using any suitable means. First signal layer 604 may be the topmost layer and may have LEDs 506 mounted thereon. Second signal layer 606 may be mounted beneath first signal layer 604. One or more LEDs 506 may be mounted upon first signal layer 604. In the embodiment of FIG. 6, there may be six mounted LEDs. However, it is contemplated that any desired number of LEDs may be mounted upon PCB 602. LEDs 506 may be spaced along PCB 602 according to any suitable pattern or arrangement. For example, the LEDs may be spaced along PCB 602 at regular intervals along a straight line. LEDs 506 may be used to illuminate bore 104 of imaging device 100 when strip 502 is mounted within ventilation channel 216 of imaging device 100.

In some embodiments, strip 502 may be arranged with minimal trace or wiring material therein. Strip 502 may be constructed without grounding layers and/or without any additional components which may require addition of signal traces. In some embodiments, the amount of trace material may be minimized according to known methods, such as by determination of the trace routing according to the Lee algorithm. Lighting circuit 210 may therefore be constructed with a minimal amount of conductive material therein. As a result, lighting circuit 210 may cause minimal or no disruption of the RF fields within bore 104 during an imaging procedure, thus minimizing increases of the SAR dose which might otherwise be caused by incorporation of lighting circuit 210 within imaging device 100.

In some alternative embodiments, trace routing of strip 502 may be discontinuous, thus forcing transition between layers of strip 502 by use of components or vias. Advantageously, such an arrangement may reduce the antenna coupling of lighting circuit 210.

In some embodiments, LEDs 506 may be "right angled" LEDs because they emit light at an angle that is parallel to the top plane of PCB 602, as compared to typical LEDs which emit light that is perpendicular to the top plane of PCB 602 and parallel to the height dimension of the PCB. When strip 502 is viewed from the front as in FIG. 6, LEDs 506 may emit light directly at the viewer, along a direction parallel to the top surface of PCB 602 and to first signal layer 604. As a result, when the strip is mounted within ventilation channel 216 of imaging device 100, LEDs 506 may have a direction of light emission that runs parallel to the longitudinal axis of bore 104. The direction of light radiating from the right-angled LEDs 506 is shown in FIG. 7. As a result, light from LEDs 506 may illuminate evenly along the entire length of bore 104. Placing LEDs 506 in bore 104 may allow for more light to be visible to the patient within bore 104 than would be supplied by a light guide from a light source placed outside the bore. This may also allow the entire bore to be visible to the patient, who may experience an enhanced calming effect because no portion of the bore is dark.

In some alternative embodiments, LEDS 506 may emit light in a direction which is perpendicular to the top plane of PCB 602. Referring to FIG. 7, strip 502 according to these embodiments may emit light in an upward direction, along an axis which is parallel to the height dimension of PCB 602. According to these embodiments, strip 502 may be situated within ventilation channel 216 with light guides or mirrors to direct the emitted light along the length of bore 104. Alternatively, strip 502 may be positioned within ventilation channel 216 in a "sideways" configuration, with the height dimension of PCB 602 being arranged parallel to the longitudinal axis of bore 104. In such embodiments, light emitted by PCB 602 may be directed parallel to the longitudinal axis of bore 104 without use of mirrors or light guides.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

It is intended that the specification and examples be considered as exemplary only, with a true scope of the invention is indicated by the following claims and their equivalents. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The invention claimed is:

1. A medical imaging device for imaging a patient during a medical imaging process, the medical imaging device comprising:
   a housing including:
   a bore extending in a lateral direction between a proximal end and a distal end, wherein the bore is configured to accommodate at least a portion of the patient extending in the lateral direction during the medical imaging process, wherein a cross-section of the bore has a circumference defined by a bore wall;
   an imager configured to generate images of the patient as the patient extends in the lateral direction within the bore;
   a ventilation channel located at the proximal end and/or the distal end of the bore and formed between a first duct portion and a second duct portion, the ventilation channel comprising an air inlet at a first end and an outlet at a second end, the outlet having an opening into the bore, wherein the opening extends around at least a portion of the bore circumference; and
   at least one lighting circuit, positioned between the first duct portion and second duct portion at the opening of the ventilation channel and positioned radially inwards from the bore wall, and wherein the at least one lighting circuit is configured to illuminate the bore, wherein the ventilation channel is configured to allow air to pass through the ventilation channel and over the at least one lighting circuit, wherein the at least one lighting circuit comprises one or more light emitting diodes having a direction of light emission that is substantially parallel to the lateral direction.

2. A medical imaging device in accordance with claim 1, wherein the at least one lighting circuit extends along an entire circumferential length of the ventilation channel.

3. A medical imaging device in accordance with claim 1, wherein an entirety of the at least one lighting circuit is positioned within a profile of the ventilation channel.

4. A medical imaging device in accordance with claim 1, further comprising:
   a coil positioned within the housing, wherein the coil at least partially surrounds the bore, and
   wherein the at least one lighting circuit is positioned distal to the distal end of the coil along the lateral direction.

5. A medical imaging device in accordance with claim 1, further comprising:
   a coil positioned within the housing, wherein the coil at least partially surrounds the bore, and
   wherein the at least one lighting circuit is positioned proximal of the proximal end of the coil along the lateral direction.

6. A medical imaging device in accordance with claim 1, wherein the at least one lighting circuit comprises one or more light emitting diodes mounted on a printed circuit board, and
   wherein light emitted by at least one light emitting diode is directed along an axis which is parallel to the lateral direction.

7. A medical imaging device in accordance with claim 6, wherein the printed circuit board comprises a plurality of signal layers and is devoid of ground layers.

8. A medical imaging device in accordance with claim 1,
   wherein the at least one lighting circuit comprises a plurality of modules, each module comprising one or more light sources and a filter, the filter having a stopband and being connected between light sources of two adjacent modules; and
   wherein a resonance frequency of the imager is within the stopband of at least one filter.

9. A medical imaging device in accordance with claim 1, wherein the ventilation channel is configured to allow passage of air from an internal volume of the housing to the bore.

10. A medical imaging device in accordance with claim 9, wherein the passage of air between the bore and the internal volume provides cooling for the lighting circuit.

11. A medical imaging device in accordance with claim 1, wherein the imager is a magnetic resonance imaging device.

12. A medical imaging device in accordance with claim 11, wherein the magnetic resonance imaging device is configured for use in combination with a radiotherapy device.

13. A medical imaging device in accordance with claim 1, wherein one or both of the proximal and distal ends of the bore along the lateral direction includes a tapered wall which reflects light into the bore.

14. A medical imaging device in accordance with claim 1 wherein the one or more light emitting diodes are mounted on a printed circuit board, and wherein at least one light emitting diode has a direction of light emission that is parallel to a plane of the printed circuit.

15. A lighting circuit positioned within a ventilation channel of a medical imaging device comprising a bore extending in a lateral direction between a proximal end and a distal end, a ventilation channel located at the proximal end and/or the distal end of the bore and formed between a first duct portion and a second duct portion, the ventilation channel comprising an air inlet at a first end and an outlet at a second end, the outlet having an opening into the bore, wherein the opening extends around at least a portion of a circumference of the bore, wherein the lighting circuit is positioned between the first duct portion and second duct portion at the opening of the ventilation channel and comprises:
   one or more light emitting diodes having a direction of light emission that is parallel to a plane of a printed circuit board and wherein the lighting circuit is positioned radially inwards from a bore wall.

16. A lighting circuit in accordance with claim 15 comprising a printed circuit board, wherein the one or more light emitting diodes are mounted on the printed circuit board and at least one light emitting diode has a direction of light emission that is parallel to the plane of the printed circuit board.

17. A lighting circuit in accordance with claim 16,
   wherein a cross-section of the bore has a circumference; and
   wherein the ventilation channel has an opening within the bore, the opening extending around at least a portion of the circumference of the bore.

18. A lighting circuit in accordance with claim 16, wherein an entire length of the bore along the lateral direction is illuminated by the light emitting diodes.

19. A lighting circuit in accordance with claim 16, wherein the ventilation channel is configured to allow passage of air from an internal volume of the medical imaging device to the bore.

20. A lighting circuit in accordance with claim 19, wherein the passage of air between the bore and the internal volume provides cooling for the lighting circuit.

* * * * *